US007776907B2

(12) United States Patent
Zeldis

(10) Patent No.: US 7,776,907 B2
(45) Date of Patent: Aug. 17, 2010

(54) METHODS FOR THE TREATMENT AND MANAGEMENT OF MACULAR DEGENERATION USING CYCLOPROPYL-N-{2-[(1S)-1-(3-ETHOXY-4-METHOXYPHENYL)-2-(METHYLSULFONYL)ETHYL]-3-OXOISOINDOLINE-4-YL}CARBOXAMIDE

(75) Inventor: Jerome B. Zeldis, Princeton, NJ (US)

(73) Assignee: Celgene Corporation, Warren, NJ (US)

( * ) Notice: Subject to any disclaimer, the term of this patent is extended or adjusted under 35 U.S.C. 154(b) by 1183 days.

(21) Appl. No.: 10/699,110

(22) Filed: Oct. 30, 2003

(65) Prior Publication Data
US 2004/0091454 A1 May 13, 2004

Related U.S. Application Data

(60) Provisional application No. 60/422,900, filed on Oct. 31, 2002.

(51) Int. Cl.
A61K 31/40 (2006.01)
(52) U.S. Cl. .................................... 514/418; 514/912
(58) Field of Classification Search ................ 514/418, 514/912
See application file for complete search history.

(56) References Cited

U.S. PATENT DOCUMENTS

| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,463,063 | A | 10/1995 | Muller |
| 5,591,767 | A | 1/1997 | Mohr et al. |
| 5,605,914 | A | 2/1997 | Muller |
| 5,632,984 | A | 5/1997 | Wong et al. |
| 5,639,476 | A | 6/1997 | Oshlack et al. |
| 5,658,940 | A | 8/1997 | Muller et al. |
| 5,674,533 | A | 10/1997 | Santus et al. |
| 5,698,579 | A | 12/1997 | Muller |
| 5,703,098 | A | 12/1997 | Muller |
| 5,728,844 | A | 3/1998 | Muller |
| 5,728,845 | A | 3/1998 | Muller |
| 5,733,566 | A | 3/1998 | Lewis |
| 5,736,570 | A | 4/1998 | Muller |
| 5,770,589 | A | 6/1998 | Billson |
| 5,801,195 | A | 9/1998 | Muller et al. |
| 5,877,200 | A | 3/1999 | Muller |
| 5,929,117 | A | 7/1999 | Muller et al. |
| 5,968,945 | A | 10/1999 | Muller et al. |
| 6,001,368 | A | 12/1999 | Jenks |
| 6,011,050 | A | 1/2000 | Muller et al. |
| 6,015,803 | A | 1/2000 | Wirostko |
| 6,020,358 | A * | 2/2000 | Muller et al. ............... 514/411 |
| 6,046,221 | A | 4/2000 | Muller et al. |
| 6,114,321 | A | 9/2000 | Platzek et al. |
| 6,130,226 | A | 10/2000 | Muller et al. |
| 6,180,644 | B1 | 1/2001 | Muller et al. |
| 6,200,987 | B1 | 3/2001 | Muller |
| 6,214,857 | B1 | 4/2001 | Muller et al. |
| 6,218,369 | B1 | 4/2001 | Bombardelli et al. |
| 6,225,348 | B1 | 5/2001 | Paulson |
| 6,235,756 | B1 * | 5/2001 | D'Amato .................... 514/323 |
| 6,262,101 | B1 | 7/2001 | Muller et al. |
| 6,284,780 | B1 | 9/2001 | Muller et al. |
| 6,326,388 | B1 | 12/2001 | Man et al. |
| 6,428,787 | B1 * | 8/2002 | Tobinick .................. 424/134.1 |
| 6,429,221 | B1 | 8/2002 | Muller et al. |
| 6,479,554 | B2 | 11/2002 | Muller et al. |
| 6,518,281 | B2 | 2/2003 | Muller et al. |
| 6,656,964 | B2 | 12/2003 | Muller et al. |
| 6,667,316 | B1 | 12/2003 | Muller et al. |

FOREIGN PATENT DOCUMENTS

| CN | 1265590 | 9/2000 |
| JP | 2000-159761 | 6/2000 |
| TW | 426520 | 3/2001 |
| WO | WO 95/01348 | 1/1995 |
| WO | WO 95/03807 | 9/1995 |
| WO | WO 97/08143 | 3/1997 |
| WO | WO 97/23457 | 7/1997 |
| WO | WO 99/06041 | 2/1999 |
| WO | WO 99/58096 | 11/1999 |
| WO | WO 01/34606 | 5/2001 |
| WO | WO 01/45702 | 6/2001 |
| WO | WO 03/080048 | 10/2003 |
| WO | WO 03/080049 | 10/2003 |

OTHER PUBLICATIONS

1 Burger's Medicinal Chemistry and Drug Discovery, 172-178, 949-982 (Manfred E. Wolff ed., 5th ed. 1995).
Corral, et al., Ann. Rheum. Dis. 58:(Suppl I) 1107-1113 (1999).
Bressler, 1999, "Photodynamic therapy of subfoveal choroidal neovascularization in age-related macular degeneration with verteporfin: one-year results of 2 randomized clinical trials—TAP Report 1," Archives of Ophthalmol. 117(10):1329-1345.
Hunt, 2002, Rostaporfin (Miravant Medical Technologies) IDrugs 5(2):180-186.
Ohno-Matsui et al., 2001, "Novel mechanism for age-related macular degeneration: an equilibrium shift between the angiogenesis factors FEGF and PEDF," J. Cell. Physiol. 189(3):323-333.

(Continued)

Primary Examiner—Zohreh A Fay
(74) Attorney, Agent, or Firm—Jones Day

(57) ABSTRACT

Methods of treating, preventing and/or managing macular degeneration are disclosed. Specific embodiments encompass the administration of a selective cytokine inhibitory drug, or a pharmaceutically acceptable salt, solvate, hydrate, stereoisomer, clathrate, or prodrug thereof, alone or in combination with a second active agent and/or surgery. Pharmaceutical compositions, single unit dosage forms, and kits suitable for use in methods of the invention are also disclosed.

13 Claims, No Drawings

OTHER PUBLICATIONS

Campchiaro et al. "The pathogenesis of choroidal neovascularization in patients with age-related macular degeneration." *Mol. Vis.*, 1999; 5: 34.

Ferrara, N. Recent Prog Horm Res., 55:15-36 (2000) includes discussion on p. 35-36).

Search report, ROC (Taiwan) Patent Application No. 092130486.

Ferrara, N. Recent Progress in Hormone Research, 55:15-36 (2000).

Kaven et al. *Ophthalmologica*, 215: 284-289 (2001).

Notice for Reasons of Rejection, JP 2004-550274.

Ono, M. *Jikken Igaku*, 16(16): 2118-2122 (1998) English Abstract included.

Pieramici et al. Eye, 22: 1330-1336 (2008).

Sampaio et al. J. Exp. Med. 173: 699-703 (1991).

Search Report, Taiwan Patent Application No. 092130486, Translation included.

Wang, H. "The Progression of Angiogenesis in the Choroid." *Foreign Medicine Ophthalmology Section*, 2001, 25(5): 288-295. English Abstract Provided.

Bressler, 1999, "Photodynamic therapy of subfoveal choroidal neovascularization in age-related macular degeneration with verteporfin: one-year results of 2 randomized clinical trials - TAP Report I," Archives of Ophthalmol. 117(10):1329-1345.

Hunt, 2002, Rostaporfin (Miravant Medical Technologies) IDrugs 5(2):180-186.

Ohno-Matsui et al., 2001, "Novel mechanism for age-related macular degeneration: an equilibrium shift between the angiogenesis factors FEGF and PEDF," J. Cell. Physiol. 189(3):323-333.

1 *Burger's Medicinal Chemistry and Drug Discovery*, 172-178, 949-982 (Manfred E. Wolff ed., 5th ed. 1995).

Corral, *et al., Ann. Rheum, Dis.* 58:(Suppl I) 1107-1113 (1999).

U.S. Appl. No. 10/105,833, filed Mar. 25, 2002, Muller.
U.S. Appl. No. 10/243,927, filed Sep. 13, 2002, Muller.
U.S. Appl. No. 10/316,673, filed Dec. 11, 2002, Muller et al.
U.S. Appl. No. 60/436,975, filed Dec. 30, 2002, Muller et al.
U.S. Appl. No. 60/438,448, filed Jan. 7, 2003, Muller et al.
U.S. Appl. No. 60/438,450, filed Jan. 7, 2003, Muller et al.
U.S. Appl. No. 60/452,460, filed Mar. 5, 2003, Muller et al.
U.S. Appl. No. 60/452,460, filed Mar. 5, 2003, Muller et al.
U.S. Appl. No. 60/454,149, filed Mar. 12, 2003, Muller et al.
U.S. Appl. No. 60/454,155, filed Mar. 12, 2003, Muller et al.
U.S. Appl. No. 60/454,149, filed Mar. 12, 2003, Man et al.
U.S. Appl. No. 10/798,372, filed Mar. 12, 2003, Man et al.
U.S. Appl. No. 10/392,195, filed Mar. 19, 2003, Schafer et al.
U.S. Appl. No. 10/392,195, filed Mar. 19, 2003, Muller et al.
U.S. Appl. No. 10/462,319, filed Jun. 16, 2003, Muller et al.
U.S. Appl. No. 10/622,618, filed Jul. 17, 2003, Muller et al.
U.S. Appl. No. 10/685,942, filed Oct. 14, 2003, Man et al.
U.S. Appl. No. 10/715,184, filed Nov. 17, 2003, Muller et al.
U.S. Appl. No. 10/748,085, filed Dec. 29, 2003, Man et al.
U.S. Appl. No. 10/786,822, filed Feb. 25, 2004, Man et al.
U.S. Appl. No. 10/794,931, filed Mar. 5, 2004, Muller et al.

* cited by examiner

METHODS FOR THE TREATMENT AND MANAGEMENT OF MACULAR DEGENERATION USING CYCLOPROPYL-N-{2-[(1S)-1-(3-ETHOXY-4-METHOXYPHENYL)-2-(METHYLSULFONYL)ETHYL]-3-OXOISOINDOLINE-4-YL}CARBOXAMIDE

This application claims the benefit of U.S. provisional application No. 60/422,900 filed on Oct. 31, 2002, the entirety of which is incorporated herein by reference.

1. FIELD OF THE INVENTION

This invention relates to methods of treating, preventing and managing macular degeneration (MD) and related syndromes, which comprise the administration of selective cytokine inhibitory drugs alone or in combination with known therapeutics. The invention also relates to pharmaceutical compositions and dosing regimens. In particular, the invention encompasses the use of selective cytokine inhibitory drugs in conjunction with surgical intervention, and/or other standard therapies for macular degeneration.

2. BACKGROUND OF THE INVENTION

2.1 Pathobiology of Macular Degeneration

Macular degeneration (MD) is an eye disease that destroys central vision by damaging the macula. The macula is part of the retina, a thin layer of nerve cells that lines most of the inside of the eyeball. The nerve cells in the retina detect light and send to the brain signals about what the eye sees. The macula is near the center of the retina at the back of the eyeball and provides the clear, sharp central vision that an animal uses for focusing on what is in front of it. The rest of the retina provides side (peripheral) vision.

There are two forms of MD: atrophic ("dry") and exudative ("wet"). Riordan-Eva, P., *Eye, in Current Medical Diagnosis and Treatment*, 41 ed. 210-211 (2002). Ninety percent of patients have the dry form, while only ten percent have the wet form. However, patients with the wet form can lose up to ninety percent of their vision. DuBosar, R., *J. of Ophthalmic Nursing and Technology*, 18: 60-64 (1998).

Macular degeneration results in the presence of choroidal neovascularisation (CNVM) and/or geographic atrophy of retinal pigment epithelium (RPE) in an eye with drusen. Bird, A. C., *Surv. Ophthamol.* 39:367-74 (1995). Drusen are rounded whitish-yellowish spots in the fundus, located external to the neuroretina. Additional symptoms of MD include RPE detachment (PED) and submacular disciform scar tissue. Algvere, P. V., *Acta Ophthalmologica Scandinavica* 80:136-143 (2002).

Choroidal neovascularisation is a problem that is related to a wide variety of retinal diseases, but is most commonly associated with MD. CNVM is characterized by abnormal blood vessels stemming from the choroid (the blood vessel-rich tissue layer just beneath the retina) growing up through the retinal layers. These new vessels are very fragile and break easily, causing blood and fluid to pool within the layers of the retina. As the vessels leak, they disturb the delicate retinal tissue, causing the vision to deteriorate. The severity of the symptoms depends on the size of the CNVM and its proximity to the macula. Patients' symptoms may be very mild, such as a blurry or distorted area of vision, or more severe, such as a central blind spot.

Patients having drusen and possibly pigmentary abnormalities, but no CNVM or geographic atrophy, are generally diagnosed as having age-related maculopathy (ARM). Id. The histopathological hallmark of ARM and MD is a continuous layer of fine granular material deposited in the inner part of Bruch's membrane at the base of the RPE cells. Sarks, J. P., et al., *Eye* 2(Pt. 5):552-77 (1988). These basal deposits are though to be accumulated as waste products from the continuing RPE phagocytosis or photoreceptor outer segment material. The basal deposits lead to a thickening and decreased permeability of Bruch's membrane. It has been hypothesized that decreased water permeability impairs an exchange of nutrients, traps water and enhances the development of soft drusen and PED and eventually leads to atrophy of RPE cells. Id. However, the current overall understanding of ARM and MD pathogenesis is incomplete. Cour, M., et al., *Drugs Aging* 19:101-133 (2002).

Because MD is most prevalent in the elderly, the fastest growing segment of the population, MD is destined to become a major problem economically and socially. Macular degeneration is the most common cause of visual loss in developed countries in individuals over the age of 60. Macular degeneration has obliterated the central vision of 1.7 million Americans and another 11 million are at risk. DuBosar, R., *J. of Ophthalmic Nursing and Technology*, 18: 60-64 (1998). Currently, there is no known cure. Rhoodhooft, J., *Bull. Soc. belge Ophtalmol.* 276:83-92 (2000). Thus, there is an urgent need for effective treatments for MD.

2.2 Treatments of Age-Related Macular Degeneration

Until recently, laser photocoagulation was the only treatment routinely used for MD, and it provides only modest results. Laser photocoagulation is a type of laser surgery that uses an intense beam of light to bum small areas of the retina and the abnormal blood vessels beneath the macula. The burns form scar tissue and seal the blood vessels, keeping them from leaking under the macula. Laser photocoagulation is effective only for patients having wet MD. Furthermore, laser photocoagulation is a viable option for only about 13% of those patients. Joffe, L. et al., *International Ophthalmology Clinics* 36(2): 99-116 (1996). Laser photocoagulation does not cure wet MD, rather it sometimes slow down or prevent further loss of central vision. Without treatment, however, vision loss from wet MD may progress until a person has no remaining central vision.

The most serious drawback to laser surgery is that the laser damages some of the nerve cells in the macula that react to light, causing some vision loss. Sometimes, the vision loss resulting from surgery is as severe or worse than the vision loss resulting from no treatment. In some patients, however, laser surgery initially worsens vision, but prevents more severe loss of vision over time.

Verteporfin has recently been used to treat wet MD. Cour, M., et al., *Drugs Aging* 19:101-133 (2002). Verteporfin is a blood-vessel-blocking photoreactive dye that is administered via injection. The dye moves to the blood vessels that are responsible for the loss of sight and is then activated by shining a non-burning beam of light into the eye in the presence of oxygen. Verteporfin is transported in the plasma primarily by lipoproteins. Activated verteporfin generates highly reactive, short-lived singlet oxygen and reactive oxygen radicals, resulting in local damage to neovascular endothelium. This causes vessel occlusion. Damaged endothelium is known to release procoagulant and vasoactive factors through the lipo-oxygenase (leukotriene) and cyclo-oxygenase (eicosanoids such as thromboxane) pathways, resulting in platelet aggregation, fibrin clot formation and vasoconstriction. Verteporfin appears to somewhat preferentially accumulate in neovasculature, including choroidal neovasculature. However, animal models indicate that verteporfin also accumulates in the retina. Therefore, verteporfin administration might collaterally damage retinal structures, including the retinal pigmented epithelium and outer nuclear layer of the retina.

Another strategy currently being investigated for the treatment of MD is pharmacological antiangiogenic therapy. Cour, M., et al., *Drugs Aging* 19:101-133 (2002). However, a first clinical trial with an antiangiogenic agent, interferon-α, showed that it was ineffective at treating MD and resulted in a high rate of adverse effects. *Arch. Ophthalmol.* 115:865-72 (1997).

Intravitreal injection of triamcinolone reportedly inhibits the growth of laser-induced CNVM in monkeys, but fails to prevent severe visual loss over a one-year period in patients with MD in a randomized trial. Gillies, M. C., et al., *Invest. Ophthalmol. Vis. Sci.* 42:S522 (2001). A number of other antiangiogenic drugs are in various stages of development for use in patients with MD, including angiostatic steroids (e.g., anecortave acetate, Alcon) and vascular epidermal growth factor (VEGF) antibodies or fragments thereof. Guyer, D. R., et al., *Invest. Ophthalmol. Vis. Sci.* 42:S522 (2001). One such VEGF antibody is rhuFab. Additional new drugs for the treatment of MD include EYE101 (Eyetech Pharmaceuticals), LY333531 (Eli Lilly), Miravant and RETISERT implant (Bausch & Lomb), which exudes a steroid into the eye for up to three years.

Although new and promising strategies for the treatment of MD and related macular degenerative diseases are being investigated, there is still no effective treatment available. Accordingly, there remains a need in the art for an effective treatment for MD.

2.3 Selective Cytokine Inhibitory Drugs

Compounds referred to as SelCIDs™ (Celgene Corporation) or Selective Cytokine Inhibitory Drugs have been synthesized and tested. These compounds potently inhibit TNF-α production, and exhibit modest inhibitory effects on LPS induced IL1β and IL12. L. G. Corral, et al., *Ann. Rheum. Dis.* 58:(Suppl I) 1107-1113 (1999).

Further characterization of the selective cytokine inhibitory drugs shows that they are potent PDE4 inhibitors. PDE4 is one of the major phosphodiesterase isoenzymes found in human myeloid and lymphoid lineage cells. The enzyme plays a crucial part in regulating cellular activity by degrading the ubiquitous second messenger cAMP and maintaining it at low intracellular levels. Id. Inhibition of PDE4 activity results in increased cAMP levels leading to the modulation of LPS induced cytokines including inhibition of TNF-α production in monocytes as well as in lymphocytes.

3. SUMMARY OF THE INVENTION

This invention encompasses methods of treating and preventing macular degeneration, which comprise administering to a patient in need thereof a therapeutically or prophylactically effective amount of a selective cytokine inhibitory drug, or a pharmaceutically acceptable salt, solvate, hydrate, stereoisomer, clathrate or prodrug thereof. The invention also encompasses methods of managing MD (e.g., lengthening the time of remission) which comprise administering to a patient in need of such management a therapeutically or prophylactically effective amount of a selective cytokine inhibitory drug, or a pharmaceutically acceptable salt, solvate, hydrate, stereoisomer, clathrate, or prodrug thereof.

Another embodiment of the invention encompasses the use of a selective cytokine inhibitory drug, or a pharmaceutically acceptable salt, solvate, hydrate, stereoisomer, clathrate or prodrug thereof, in combination with another therapeutic useful to treat or prevent MD such as, but not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof.

Yet another embodiment of the invention encompasses methods for treating, preventing or managing MD, comprising administering to a patient in need thereof an effective amount of a selective cytokine inhibitory drug, or a pharmaceutically acceptable salt, solvate, hydrate, stereoisomer, clathrate or prodrug thereof, in combination with a conventional therapy used to treat or prevent MD such as, but not limited to, surgical intervention (e.g., laser photocoagulation therapy and photodynamic therapy).

The invention further encompasses pharmaceutical compositions, single unit dosage forms, and kits suitable for use in treating, preventing and/or managing MD, which comprise a selective cytokine inhibitory drug, or a pharmaceutically acceptable salt, solvate, hydrate, stereoisomer, clathrate, or prodrug thereof.

4. DETAILED DESCRIPTION OF THE INVENTION

A first embodiment of the invention encompasses methods of treating and preventing MD, which comprise administering to a patient (e.g., a mammal such as a human) in need thereof a therapeutically or prophylactically effective amount of a selective cytokine inhibitory drug or a pharmaceutically acceptable salt, solvate, hydrate, stereoisomer, clathrate or prodrug thereof. The invention further relates to the treatment or prevention of specific types of MD and related syndromes including, but not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

As used herein, the term macular degeneration (MD) encompasses all forms of macular degenerative diseases regardless of a patient's age, although some macular degenerative diseases are more common in certain age groups. These include, but are not limited to, Best's disease or vitelliform (most common in patients under about 7 years of age); Stargardt's disease, juvenile macular dystrophy or fundus flavimaculatus (most common in patients between about 5 and about 20 years of age); Behr's disease, Sorsby's disease, Doyne's disease or honeycomb dystrophy (most common in patients between about 30 and about 50 years of age); and age-related macular degeneration (most common in patients of about 60 years of age or older).

Causes of MD include, but are not limited to, genetic, physical trauma, diseases such as diabetes, and infection, such as bacterial infection (e.g., leprosy and ENL in particular).

Another embodiment of the invention encompasses methods of managing MD which comprise administering to a patient in need of such management a prophylactically effective amount of a selective cytokine inhibitory drug, or a pharmaceutically acceptable salt, solvate, hydrate, stereoisomer, clathrate, or prodrug thereof.

Another embodiment of the invention encompasses a pharmaceutical composition comprising a selective cytokine inhibitory drug, or a pharmaceutically acceptable salt, solvate, hydrate, stereoisomer, clathrate, or prodrug thereof, and an optional carrier.

Also encompassed by the invention are single unit dosage forms comprising a selective cytokine inhibitory drug, or a pharmaceutically acceptable salt, solvate, hydrate, stereoisomer, clathrate, or prodrug thereof, and an optional carrier.

Another embodiment of the invention encompasses a kit comprising: a pharmaceutical composition comprising a selective cytokine inhibitory drug, or a pharmaceutically acceptable salt, solvate, hydrate, stereoisomer, clathrate, or prodrug thereof. The invention further encompasses kits comprising single unit dosage forms. Kits encompassed by this invention can further comprise additional active agents. A specific kit comprises an Amsler grid useful for detecting or diagnosing MD.

Without being limited by theory, it is believed that certain selective cytokine inhibitory drugs and other medications that may be used to treat symptoms of MD can act in complementary or synergistic ways in the treatment or management of MD. Therefore, one embodiment of the invention encompasses a method of treating, preventing and/or managing MD, which comprises administering to a patient in need thereof a therapeutically or prophylactically effective amount of a selective cytokine inhibitory drug, or a pharmaceutically acceptable salt, solvate, hydrate, stereoisomer, clathrate, or prodrug thereof, and a therapeutically or prophylactically effective amount of a second active agent.

Examples of second active agents include, but are not limited to, conventional therapeutics used to treat or prevent MD such as steroids, light sensitizers, integrins, antioxidants, interferons, xanthine derivatives, growth hormones, neutrotrophic factors, regulators of neovascularization, anti-VEGF antibodies, prostaglandins, antibiotics, phytoestrogens, anti-inflammatory compounds and antiangiogenesis compounds, and other therapeutics found, for example, in the *Physician's Desk Reference* 2003. Specific examples of second active agents include, but are not limited to, verteporfin, purlytin, an angiostatic steroid, rhuFab, interferon-2α, an integrin, an antioxidant, and pentoxifylline.

The invention also encompasses pharmaceutical compositions, single unit dosage forms, and kits which comprise a selective cytokine inhibitory drug, or a pharmaceutically acceptable salt, solvate, hydrate, stereoisomer, clathrate, or prodrug thereof, and a second active agent. For example, a kit may contain a compound of the invention and a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof, or other drug capable of relieving or alleviating a symptom of MD.

It is believed that particular selective cytokine inhibitory drugs can reduce or eliminate adverse effects associated with the administration of therapeutic agents used to treat MD, thereby allowing the administration of larger amounts of the agents to patients and/or increasing patient compliance. Consequently, another embodiment of the invention encompasses a method of reversing, reducing or avoiding an adverse effect associated with the administration of a second active agent in a patient suffering from MD, which comprises administering to a patient in need thereof a therapeutically or prophylactically effective amount of a selective cytokine inhibitory drug, or a pharmaceutically acceptable salt, solvate, hydrate, stereoisomer, clathrate, or prodrug thereof.

As discussed elsewhere herein, symptoms of MD can be treated with surgical intervention, such as, but not limited to, light or laser therapy, radiation therapy, retinal pigment epithelium transplantation, and foveal translocation. Without being limited by theory, it is believed that the combined use of such conventional therapies and a selective cytokine inhibitory drug can be highly effective. Therefore, this invention encompasses a method of treating, preventing and/or managing MD, which comprises administering to a patient a selective cytokine inhibitory drug, or a pharmaceutically acceptable salt, solvate, hydrate, stereoisomer, clathrate, or prodrug thereof, before, during, or after surgical intervention, or other conventional, non-drug based therapies.

4.1 Selective Cytokine Inhibitory Drugs

Compounds used in the invention include racemic, stereomerically pure and stereomerically enriched selective cytokine inhibitory drugs, stereomerically and enantiomerically pure compounds that have selective cytokine inhibitory activities, and pharmaceutically acceptable salts, solvates, hydrates, stereoisomers, clathrates, and prodrugs thereof. Preferred compounds used in the invention are known Selective Cytokine Inhibitory Drugs (SelCIDs™) of Celgene Corporation, N.J.

As used herein and unless otherwise indicated, the terms. "selective cytokine inhibitory drugs" and "SelCIDs™" encompass small molecule drugs, e.g., small organic molecules which are not peptides, proteins, nucleic acids, oligosaccharides or other macromolecules. Preferred compounds inhibit TNF-α production. Compounds may also have a modest inhibitory effect on LPS induced IL1β and IL12. More preferably, the compounds of the invention are potent PDE4 inhibitors.

Specific examples of selective cytokine inhibitory drugs include, but are not limited to, the cyclic imides disclosed in U.S. Pat. Nos. 5,605,914 and 5,463,063; the cycloalkyl amides and cycloalkyl nitriles of U.S. Pat. Nos. 5,728,844, 5,728,845, 5,968,945, 6,180,644 and 6,518,281; the aryl amides (for example, an embodiment being N-benzoyl-3-amino-3-(3',4'-dimethoxyphenyl)-propanamide) of U.S. Pat. Nos. 5,801,195, 5,736,570, 6,046,221 and 6,284,780; the imide/amide ethers and alcohols (for example, 3-phthalimido-3-(3',4'-dimethoxyphenyl)propan-1-ol) disclosed in U.S. Pat. No. 5,703,098; the succinimides and maleimides (for example methyl 3-(3',4',5'6'-petrahydrophthalimdo)-3-(3",4"-dimethoxyphenyl)propionate) disclosed in U.S. Pat. No. 5,658,940; imido and amido substituted alkanohydroxamic acids disclosed in U.S. Pat. No. 6,214,857 and WO 99/06041; substituted phenethylsulfones disclosed in U.S. Pat. Nos. 6,011,050 and 6,020,358; substituted imides (for example, 2-phthalimido-3-(3+,4'-dimethoxyphenyl) propane) disclosed in U.S. Pat. No. 6,429,221; substituted 1,3, 4-oxadiazoles (for example, 2-[1-(3 -cyclopentyloxy-4-methoxyphenyl)-2-(1,3,4-oxadiazole-2-yl)ethyl]-5-methylisoindoline-1,3-dione) disclosed in U.S. Pat. No. 6,326,388; cyano and carboxy derivatives of substituted styrenes (for example, 3,3-bis-(3,4-dimethoxyphenyl) acrylonitrile) disclosed in U.S. Pat. Nos. 5,929,117, 6,130,226, 6,262, 101 and 6,479,554; isoindoline-1-one and isoindoline-1,3-dione substituted in the 2-position with an α-(3,4-disubstituted phenyl)alkyl group and in the 4- and/or 5-position with a nitrogen-containing group disclosed in WO 01/34606; and imido and amido substituted acylhydroxamic acids (for example, (3-(1,3-dioxoisoindoline-2-yl)-3-(3-ethoxy-4-methoxyphenyl) propanoylamino) propanoate disclosed in WO 01/45702. The entireties of each of the patents and patent applications identified herein are incorporated herein by reference.

Additional selective cytokine inhibitory drugs belong to a family of synthesized chemical compounds of which typical embodiments include 3-(1,3-dioxobenzo-[f]isoindol-2-yl)-3-(3-cyclopentyloxy-4-methoxyphenyl)propionamide and 3-(1,3-dioxo-4-azaisoindol-2-yl)-3-(3,4-dimethoxyphenyl)-propionamide.

Other specific selective cytokine inhibitory drugs belong to a class of non-polypeptide cyclic amides disclosed in U.S. Pat. Nos. 5,698,579 and 5,877,200, both of which are incorporated herein. Representative cyclic amides include compounds of the formula:

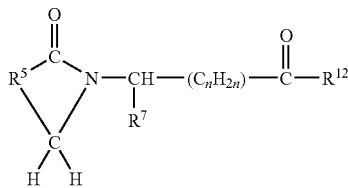

wherein n has a value of 1, 2, or 3;

$R^5$ is o-phenylene, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, and halo;

$R^7$ is (i) phenyl or phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, (ii) benzyl unsubstituted or substituted with 1 to 3 substituents selected from the group consisting of nitro, cyano, trifluoromethyl, carbothoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, (iii) naphthyl, and (iv) benzyloxy;

$R^{12}$ is —OH, alkoxy of 1 to 12 carbon atoms, or

$R^8$ is hydrogen or alkyl of 1 to 10 carbon atoms; and $R^9$ is hydrogen, alkyl of 1 to 10 carbon atoms, —COR$^{10}$, or —SO$_2$R$^{10}$, wherein R$^{10}$ is hydrogen, alkyl of 1 to 10 carbon atoms, or phenyl.

Specific compounds of this class include, but are not limited to:

3-phenyl-2-(1-oxoisoindolin-2-yl)propionic acid;
3-phenyl-2-(1-oxoisoindolin-2-yl)propionamide;
3-phenyl-3-(1-oxoisoindolin-2-yl)propionic acid;
3-phenyl-3-(1-oxoisoindolin-2-yl)propionamide;
3-(4-methoxyphenyl)-3-(1-oxisoindolin-yl)propionic acid;
3-(4-methoxyphenyl)-3-(1-oxisoindolin-yl)propionamide;
3-(3,4-dimethoxyphenyl)-3-(1-oxisoindolin-2-yl)propionic acid;
3-(3,4-dimethoxy-phenyl)-3-(1-oxo-1,3-dihydroisoindol-2-yl)propionamide;
3-(3,4-dimethoxyphenyl)-3-(1-oxisoindolin-2-yl)propionamide;
3-(3,4-diethoxyphenyl)-3-(1-oxoisoindolin-yl)propionic acid;
methyl 3-(1-oxoisoindolin-2-yl)-3-(3-ethoxy-4-methoxyphenyl)propionate;
3-(1-oxoisoindolin-2-yl)-3-(3-ethoxy-4-methoxyphenyl)propionic acid;
3-(1-oxoisoindolin-2-yl)-3-(3-propoxy-4-methoxyphenyl)propionic acid;
3-(1-oxoisoindolin-2-yl)-3-(3-butoxy-4-methoxyphenyl)propionic acid;
3-(1-oxoisoindolin-2-yl)-3-(3-propoxy-4-methoxyphenyl)propionamide;
3-(1-oxoisoindolin-2-yl)-3-(3-butoxy-4-methoxyphenyl)propionamide;
methyl 3-(1-oxoisoindolin-2-yl)-3-(3-butoxy-4-methoxyphenyl)propionate; and
methyl 3-(1-oxoisoindolin-2-yl)-3-(3-propoxy-4-methoxyphenyl)propionate.

Other specific selective cytokine inhibitory drugs include the imido and amido substituted alkanohydroxamic acids disclosed in WO 99/06041, which is incorporated herein by reference. Examples of such compound include, but are not limited to:

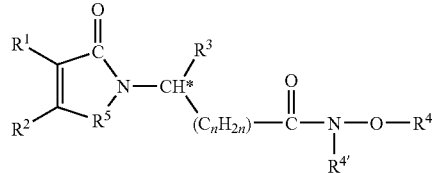

wherein each of $R^1$ and $R^2$, when taken independently of each other, is hydrogen, lower alkyl, or $R^1$ and $R^2$, when taken together with the depicted carbon atoms to which each is bound, is o-phenylene, o-naphthylene, or cyclohexene-1,2-diyl, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, and halo;

$R^3$ is phenyl substituted with from one to four substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, alkylthio of 1 to 10 carbon atoms, benzyloxy, cycloalkoxy of 3 to 6 carbon atoms, $C_4$-$C_6$-cycloalkylidenemethyl, $C_3$-$C_{10}$-alkylidenemethyl, indanyloxy, and halo;

$R^4$ is hydrogen, alkyl of 1 to 6 carbon atoms, phenyl, or benzyl;

$R^{4'}$ is hydrogen or alkyl of 1 to 6 carbon atoms;

$R^5$ is —CH$_2$—, —CH$_2$—CO—, —SO$_2$—, —S—, or —NHCO—;

n has a value of 0, 1, or 2; and the acid addition salts of said compounds which contain a nitrogen atom capable of being protonated.

Additional specific selective cytokine inhibitory drugs used in the invention include, but are not limited to:

3-(3-ethoxy-4-methoxyphenyl)-N-hydroxy-3-(1-oxoisoindolinyl)propionamide;

3-(3-ethoxy-4-methoxyphenyl)-N-methoxy-3-(1-oxoisoindolinyl)propionamide;

N-benzyloxy-3-(3-ethoxy-4-methoxyphenyl)-3-phthalimidopropionamide;

N-benzyloxy-3-(3-ethoxy-4-methoxyphenyl)-3-(3-nitrophthalimido)propionamide;

N-benzyloxy-3-(3-ethoxy-4-methoxyphenyl)-3-(1-oxoisoindolinyl)propionamide;

3-(3-ethoxy-4-methoxyphenyl)-N-hydroxy-3-phthalimidopropionamide;

N-hydroxy-3-(3,4-dimethoxyphenyl)-3-phthalimidopropionamide;

3-(3-ethoxy-4-methoxyphenyl)-N-hydroxy-3-(3-nitrophthalimido)propionamide;

N-hydroxy-3-(3,4-dimethoxyphenyl)-3-(1-oxoisoindolinyl)propionamide;

3-(3-ethoxy-4-methoxyphenyl)-N-hydroxy-3-(4-methylphthalimido)propionamide;

3-(3-cyclopentyloxy-4-methoxyphenyl)-N-hydroxy-3-phthalimidopropionamide;

3-(3-ethoxy-4-methoxyphenyl)-N-hydroxy-3-(1,3-dioxo-2,3-dihydro-1H-benzo[f]isoindol-2-yl)propionamide;

N-hydroxy-3-{3-(2-propoxy)-4-methoxyphenyl}-3-phthalimidopropionamide;

3-(3-ethoxy-4-methoxyphenyl)-3-(3,6-difluorophthalimido)-N-hydroxypropionamide;

3-(4-aminophthalimido)-3-(3-ethoxy-4-methoxyphenyl)-N-hydroxypropionamide;

3-(3-aminophthalimido)-3-(3-ethoxy-4-methoxyphenyl)-N-hydroxypropionamide;

N-hydroxy-3-(3,4-dimethoxyphenyl)-3-(1-oxoisoindolinyl)propionamide;

3-(3-cyclopentyloxy-4-methoxyphenyl)-N-hydroxy-3-(1-oxoisoindolinyl) propionamide; and N-benzyloxy-3-(3-ethoxy-4-methoxyphenyl)-3-(3-nitrophthalimido)propionamide.

Additional selective cytokine inhibitory drugs used in the invention include the substituted phenethylsulfones substituted on the phenyl group with a oxoisoindine group. Examples of such compounds include, but are not limited to, those disclosed in U.S. Pat. No. 6,020,358, which is incorporated herein, which include the following:

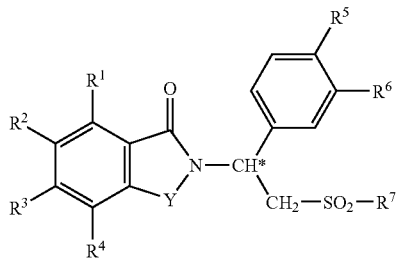

wherein the carbon atom designated * constitutes a center of chirality;

Y is C=O, CH$_2$, SO$_2$, or CH$_2$C=O; each of R$^1$, R$^2$, R$^3$, and R$^4$, independently of the others, is hydrogen, halo, alkyl of 1 to 4 carbon atoms, alkoxy of 1 to 4 carbon atoms, nitro, cyano, hydroxy, or —NR$^8$R$^9$; or any two of R$^1$, R$^2$, R$^3$, and R$^4$ on adjacent carbon atoms, together with the depicted phenylene ring are naphthylidene;

each of R$^5$ and R$^6$, independently of the other, is hydrogen, alkyl of 1 to 4 carbon atoms, alkoxy of 1 to 4 carbon atoms, cyano, or cycloalkoxy of up to 18 carbon atoms;

R$^7$ is hydroxy, alkyl of 1 to 8 carbon atoms, phenyl, benzyl, or NR$^{8'}$R$^{9'}$;

each of R$^8$ and R$^9$ taken independently of the other is hydrogen, alkyl of 1 to 8 carbon atoms, phenyl, or benzyl, or one of R$^8$ and R$^9$ is hydrogen and the other is —COR$^{10}$ or —SO$_2$R$^{10}$, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and each of R$^{8'}$ and R$^{9'}$ taken independently of the other is hydrogen, alkyl of 1 to 8 carbon atoms, phenyl, or benzyl, or one of R$^{8'}$ and R$^{9'}$ is hydrogen and the other is —COR$^{10'}$ or —SO$_2$R$^{10'}$, or R$^{8'}$ and R$^{9'}$ taken together are tetramethylene, pentamethylene, hexamethylene, or —CH$_2$CH$_2$X$^2$CH$_2$CH$_2$— in which X$^2$ is —O—, —S—, or —NH—.

It will be appreciated that while for convenience the above compounds are identified as phenethylsulfones, they include sulfonamides when R$^7$ is NR$^{8'}$R$^{9'}$.

Specific groups of such compounds are those in which Y is C=O or CH$_2$.

A further specific group of such compounds are those in which each of R$^1$, R$^2$, R$^3$, and R$^4$ independently of the others, is hydrogen, halo, methyl, ethyl, methoxy, ethoxy, nitro, cyano, hydroxy, or —NR$^8$R$^9$ in which each of R$^8$ and R$^9$ taken independently of the other is hydrogen or methyl or one of R$^8$ and R$^9$ is hydrogen and the other is —COCH$_3$.

Particular compounds are those in which one of R$^1$, R$^2$, R$^3$, and R$^4$ is —NH$_2$ and the remaining of R$^1$, R$^2$, R$^3$, and R$^4$ are hydrogen.

Particular compounds are those in which one of R$^1$, R$^2$, R$^3$, and R$^4$ is —NHCOCH$_3$ and the remaining of R$^1$, R$^2$, R$^3$, and R$^4$ are hydrogen.

Particular compounds are those in which one of R$^1$, R$^2$, R$^3$, and R$^4$ is —N(CH$_3$)$_2$ and the remaining of R$^1$, R$^2$, R$^3$, and R$^4$ are hydrogen.

A further preferred group of such compounds are those in which one of R$^1$, R$^2$, R$^3$, and R$^4$ is methyl and the remaining of R$^1$, R$^2$, R$^3$, and R$^4$ are hydrogen.

Particular compounds are those in which one of R$^1$, R$^2$, R$^3$, and R$^4$ is fluoro and the remaining of R$^1$, R$^2$, R$^3$, and R$^4$ are hydrogen.

Particular compounds are those in which each of R$^5$ and R$^6$, independently of the other, is hydrogen, methyl, ethyl, propyl, methoxy, ethoxy, propoxy, cyclopentoxy, or cyclohexoxy.

Particular compounds are those in which R$^5$ is methoxy and R$^6$ is monocycloalkoxy, polycycloalkoxy, and benzocycloalkoxy.

Particular compounds are those in which R$^5$ is methoxy and R$^6$ is ethoxy.

Particular compounds are those in which R$^7$ is hydroxy, methyl, ethyl, phenyl, benzyl, or NR$^{8'}$R$^{9'}$ in which each of R$^{8'}$ and R$^{9'}$ taken independently of the other is hydrogen or methyl.

Particular compounds are those in which R$^7$ is methyl, ethyl, phenyl, benzyl or NR$^{8'}$R$^{9'}$ in which each of R$^{8'}$ and R$^{9'}$ taken independently of the other is hydrogen or methyl.

Particular compounds are those in which R$^7$ is methyl.

Particular compounds are those in which $R^7$ is $NR^{8'}R^{9'}$ in which each of $R^{8'}$ and $R^{9'}$ taken independently of the other is hydrogen or methyl.

Other specific selective cytokine inhibitory drugs include fluoroalkoxy-substituted 1,3-dihydro-isoindolyl compounds found in U.S. Provisional Application No. 60/436,975 to G. Muller et al., filed Dec. 30, 2002, which is incorporated herein in its entirety by reference. Representative fluoroalkoxy-substituted 1,3-dihydro-isoindolyl compounds include compounds of the formula:

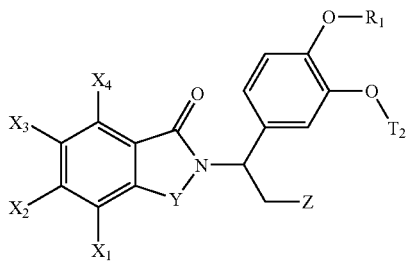

wherein:

Y is —C(O)—, —CH$_2$, —CH$_2$C(O)—, —C(O)CH$_2$—, or SO$_2$;

Z is —H, —C(O)R$^3$, —(C$_{0-1}$-alkyl)-SO$_2$-(C$_{1-4}$-alkyl), —C$_{1-8}$-alkyl, —CH$_2$OH, CH$_2$(O)(C$_{1-8}$alkyl) or —CN;

R$_1$ and R$_2$ are each independently —CHF$_2$, —C$_{1-8}$-alkyl, —C$_{3-18}$-cycloalkyl, or —(C$_{1-10}$-alkyl)(C$_{3-18}$-cycloalkyl), and at least one of R$_1$ and R$_2$ is CHF$_2$;

R$^3$ is —NR$^4$R$^5$, -alkyl, —OH, —O-alkyl, phenyl, benzyl, substituted phenyl, or substituted benzyl;

R$^4$ and R$^5$ are each independently —H, —C$_{1-8}$-alkyl, —OH, —OC(O)R$^6$;

R is —C$_{1-8}$-alkyl, -amino(C$_{1-8}$-alkyl), -phenyl, -benzyl, or -aryl;

X$_1$, X$_2$, X$_3$, and X$_4$ are each independent -H, -halogen, -nitro, —NH$_2$, —CF$_3$, —C$_{1-6}$-alkyl, —(C$_{0-4}$-alkyl)-(C$_{3-6}$-cycloalkyl), (C$_{0-4}$-alkyl)-NR$^7$R$^8$, (C$_{0-4}$-alkyl)-N(H)C(O)—(R$^8$), (C$_{0-4}$-alkyl)-N(H)C(O)N(R$^7$R$^8$), (C$_{0-4}$-alkyl)-N(H)C(O)O(R$^7$R$^8$), (C$_{0-4}$-alkyl)-OR$^8$, (C$_{0-4}$-alkyl)-imidazolyl, (C$_{0-4}$-alkyl)-pyrrolyl, (C$_{0-4}$-alkyl)-oxadiazolyl, or (C$_{0-4}$-alkyl)-triazolyl, or two of X$_1$, X$_2$, X$_3$, and X$_4$ may be joined together to form a cycloalkyl or heterocycloalkyl ring, (e.g., X$_1$ and X$_2$, X$_2$ and X$_3$, X$_3$ and X$_4$, X$_1$ and X$_3$, X$_2$ and X$_4$, or X$_1$ and X$_4$ may form a 3, 4, 5, 6, or 7 membered ring which may be aromatic, thereby forming a bicyclic system with the isoindolyl ring); and R$^7$ and R$^8$ are each independently H, C$_{1-9}$-alkyl, C$_{3-6}$-cycloalkyl, (C$_{1-6}$-alkyl)-(C$_{3-6}$-cycloalkyl), (C$_{1-6}$-alkyl)-N(R$^7$R$^8$), (C$_{1-6}$-alkyl)-OR$^8$, phenyl, benzyl, or aryl;

or a pharmaceutically acceptable salt, solvate, hydrate, stereoisomer, clathrate, or prodrug thereof.

Preferred compounds of the invention include, but are not limited to:

3-(4-Acetylamino-1,3-dioxo-1,3-dihydro-isoindol-2-yl)-3-(3-cyclopropylmethoxy-4-difluoromethoxy-phenyl)-propionic acid;

3-(4-Acetylamino-1,3-dioxo-1,3-dihydro-isoindol-2-yl)-3-(3-cyclopropylmethoxy-4-difluoromethoxy-phenyl)-N,N-dimethyl-propionamide;

3-(4-Acetylamino-1,3-dioxo-1,3-dihydro-isoindol-2-yl)-3-(3 cyclopropylmethoxy-4-difluoromethoxy-phenyl)-propionamide;

3-(3-Cyclopropylmethoxy-4-difluoromethoxy-phenyl)-3-(1,3-dioxo-1,3-dihydro-isoindol-2-yl)-propionic acid;

3-(3-Cyclopropylmethoxy-4-difluoromethoxy-phenyl)-3-(1,3-dioxo-1,3-dihydro-isoindol-2-yl)-N-hydroxy-propionamide;

3-(3-Cyclopropylmethoxy-4-difluoromethoxy-phenyl)-3-(7-nitro-1-oxo-1,3-dihydro-isoindol-2-yl)-propionic acid methyl ester;

3-(3-Cyclopropylmethoxy-4-difluoromethoxy-phenyl)-3-(7-nitro-1-oxo-1,3-dihydro-isoindol-2-yl)-propionic acid;

3-(3-Cyclopropylmethoxy-4-difluoromethoxy-phenyl)-3-(7-nitro-1-oxo-1,3-dihydro-isoindol-2-yl)-)-N,N-dimethyl-propionamide;

3-(7-Amino-1-oxo-1,3-dihydro-isoindol-2-yl)-3-(3-cyclopropylmethoxy-4-difluoromethoxy-phenyl)-N,N-dimethyl-propionamide;

3-(4-Difluoromethoxy-3-ethoxy-phenyl)-3-(7-nitro-1-oxo-1,3-dihydro-isoindol-2-yl)-propionic acid methyl ester;

3-(7-Amino-1-oxo-1,3-dihydro-isoindol-2-yl)-3-(4-difluoromethoxy-3-ethoxy-phenyl)-propionic acid methyl ester;

3-[7-(Cyclopropanecarbonyl-amino)-1-oxo-1,3-dihydro-isoindol-2-yl]-3-(4-difluoromethoxy-3-ethoxy-phenyl)-propionic acid methyl ester;

3-(7-Acetylamino-1-oxo-1,3-dihydro-isoindol-2-yl)-3-(4-difluoromethoxy-3-ethoxy-phenyl)-propionic acid methyl ester;

3-(7-Acetylamino-1-oxo-1,3-dihydro-isoindol-2-yl)-3-(4-difluoromethoxy-3-ethoxy-phenyl)-propionic acid;

3-[7-(Cyclopropanecarbonyl-amino)-1-oxo-1,3-dihydro-isoindol-2-yl]-3-(4-difluoromethoxy-3-ethoxy-phenyl)-propionic acid;

Cyclopropanecarboxylic acid {2-[2-carbamoyl-1-(4-difluoromethoxy-3-ethoxy-phenyl)-ethyl]-3-oxo-2,3-dihydro-1H-isoindol-4-yl}-amide;

Cyclopropanecarboxylic acid {2-[1-(4-difluoromethoxy-3-ethoxy-phenyl)-2-dimethylcarbamoyl-ethyl]-3-oxo-2,3-dihydro-1H-isoindol-4-yl}-;

Cyclopropanecarboxylic acid {2-[1-(4-difluoromethoxy-3-ethoxy-phenyl)-2-hydroxycarbamoyl-ethyl]-3-oxo-2,3-dihydro-1H-isoindol-4-yl}-amide;

3-(7-Acetylamino-1-oxo-1,3-dihydro-isoindol-2-yl)-3-(4-difluoromethoxy-3-ethoxy-phenyl)-propionamide;

3-(7-Acetylamino-1-oxo-1,3-dihydro-isoindol-2-yl)-3-(4-difluoromethoxy-3-ethoxy-phenyl)-N,N-dimethyl-propionamide;

3-(7-Acetylamino-1-oxo-1,3-dihydro-isoindol-2-yl)-3-(4-difluoromethoxy-3-ethoxy-phenyl)-N-hydroxy-propionamide;

3-(4-Acetylamino-1,3-dioxo-1,3-dihydro-isoindol-2-yl)-3-(4-difluoromethoxy-3-ethoxy-phenyl)-propionic acid;

3-(4-Acetylamino-1,3-dioxo-1,3-dihydro-isoindol-2-yl)-3-(4-difluoromethoxy-3-ethoxy-phenyl)-propionamide;

3-(4-Acetylamino-1,3-dioxo-1,3-dihydro-isoindol-2-yl)-3-(4-difluoromethoxy-3-ethoxy-phenyl)-N,N-dimethyl-propionamide;

3-(4-Acetylamino-1,3-dioxo-1,3-dihydro-isoindol-2-yl)-3-(4-difluoromethoxy-3-ethoxy-phenyl)-N-hydroxy-propionamide;

Cyclopropanecarboxylic acid {2-[1-(4-difluoromethoxy-3-ethoxy-phenyl)-2-methanesulfonyl-ethyl]-3-oxo-2,3-dihydro-1H-isoindol-4-yl}-amide;

N-{2-[1-(4-Difluoromethoxy-3-ethoxy-phenyl)-2-methanesulfonyl-ethyl]-1,3-dioxo-2,3-dihydro-1H-isoindol-4-yl}-acetamide; and Cyclopropanecarboxylic acid {2-[2-carbamoyl-1-(4-difluoromethoxy-3-ethoxy-phenyl)-ethyl]-7-chloro-3-oxo-2,3-dihydro-1H-isoindol-4-yl}-amide.

Other selective cytokine inhibitory drugs include 7-amido-substituted isoindolyl compounds found in U.S. Provisional Application No. 60/454,155 to G. Muller et al., filed Mar. 12, 2003, which is incorporated herein in its entirety by reference. Representative 7-amido-substituted isoindolyl compounds include compounds of the formula:

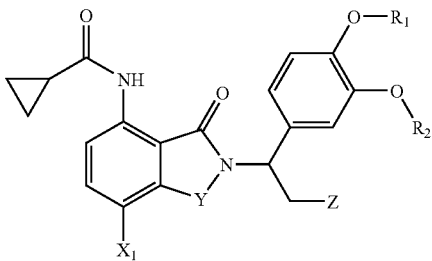

wherein:
Y is —C(O)—, —CH$_2$—, —CH$_2$C(O)— or SO$_2$;
X is H;
Z is (C$_{0-4}$-alkyl)-C(O)R$^3$, C$_{1-4}$-alkyl, (C$_{0-4}$-alkyl)-OH, (C$_{1-4}$-alkyl)-O(C$_{1-4}$-alkyl), (C$_{1-4}$-alkyl)-SO$_2$(C$_{1-4}$-alkyl), (C$_{0-4}$-alkyl)-SO(C$_{1-4}$-alkyl), (C$_{0-4}$-alkyl)-NH$_2$, (C$_{0-4}$-alkyl)-N(C$_{1-8}$-alkyl)$_2$, (C$_{0-4}$-alkyl)-N(H)(OH), CH$_2$NSO$_2$(C$_{1-4}$-alkyl);
R$_1$ and R$_2$ are independently C$_{1-8}$-alkyl, cycloalkyl, or (C$_{1-4}$-alkyl)cycloalkyl;
R$^3$ is, NR$^4$R$^5$, OH, or O—(C$_{1-8}$-alkyl);
R$^4$ is H;
R$^5$ is —OH, or —OC(O)R$^6$;
R$^6$ is C$_{1-8}$-alkyl, amino-(C$_{1-8}$-alkyl), (C$_{1-8}$-alkyl)-(C$_{3-6}$-cycloalkyl), C$_{3-6}$cycloalkyl, phenyl, benzyl, or aryl;
or a pharmaceutically acceptable salt, solvate, hydrate, stereoisomer, clathrate, or prodrug thereof; or the formula:

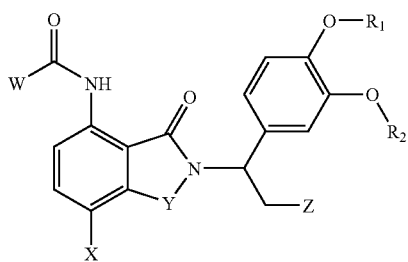

wherein:
Y is —C(O)—, —CH$_2$—, —CH$_2$C(O)—, or SO$_2$;
X is halogen, —CN, —NR$_7$R$_8$, —NO$_2$, or —CF$_3$,
W is

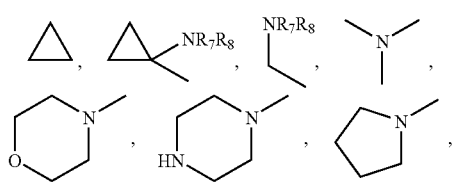

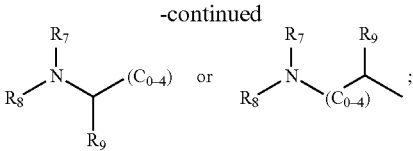

Z is (C$_{0-4}$alkyl)-SO$_2$(C$_{1-4}$-alkyl), —(C$_{0-4}$alkyl)-CN, —(C$_{0-4}$alkyl)-C(O)R$^3$, C$_{1-4}$-alkyl, (C$_{0-4}$-alkyl)OH, (C$_{0-4}$-alkyl)O(C$_{1-4}$-alkyl), (C$_{0-4}$-alkyl)SO(C$_{1-4}$-alkyl), (C$_{0-4}$-alkyl)NH$_2$, (C$_{0-4}$-alkyl)N(C$_{1-8}$-alkyl)$_2$, (C$_{0-4}$-alkyl) N(H)(OH), or (C$_{0-4}$-alkyl)NSO$_2$(C1-4-alkyl);
W is —C$_{3-6}$-cycloalkyl, —(C$_{1-8}$-alkyl)-(C$_{3-6}$-cycloalkyl), —(C$_{0-8}$-alkyl)-(C$_{3-6}$cycloalkyl)-NR$_7$R$_8$, (C$_{0-8}$-alkyl)-NR$_7$R$_8$, (C$_{0-4}$-alkyl)-CHR$_9$—(C$_{0-4}$-alkyl)-NR$_7$R$_8$;
R$_1$ and R$_2$ are independently C$_{1-8}$-alkyl, cycloalkyl, or (C$_{1-4}$-alkyl)cycloalkyl;
R$^3$ is C$_{1-8}$-alkyl, NR$^4$R$^5$, OH, or O—(C$_{1-8}$-alkyl);
R$^4$ and R$^5$ are independently H, C$_{1-8}$-alkyl, (C$_{0-8}$-alkyl)-(C$_{3-6}$-cycloalkyl), OH, or —OC(O)R$^6$;
R$^6$ is C$_{1-8}$-alkyl, (C$_{0-8}$-alkyl)-(C$_{3-6}$-cycloalkyl), amino-(C$_{1-8}$-alkyl), phenyl, benzyl, or aryl;
R$_7$ and R$_8$ are each independently H, C$_{1-8}$-alkyl, (C$_{0-8}$alkyl)-(C$_{3-6}$-cycloalkyl), phenyl, benzyl, aryl, or can be taken together with the atom connecting them to form a 3 to 7 membered heterocycloalkyl or heteroaryl ring;
R$_9$ is C$_{1-4}$-alkyl, (C$_{0-4}$-alkyl)aryl, (C$_{0-4}$-alkyl)-(C$_{3-6}$-cycloalkyl), (C$_{0-4}$-alkyl)-heterocylcle; or
a pharmaceutically acceptable salt, solvate, hydrate, stereoisomer, clathrate, or prodrug thereof.

Still other selective cytokine inhibitory drugs include N-alkyl-hydroxamic acid-isoindolyl compounds found in U.S. Provisional Application No. 60/454,149 to G. Muller et al., filed Mar. 12, 2003, which is incorporated herein in its entirety by reference. Representative N-alkyl-hydroxamic acid-isoindolyl compounds include compounds of the formula:

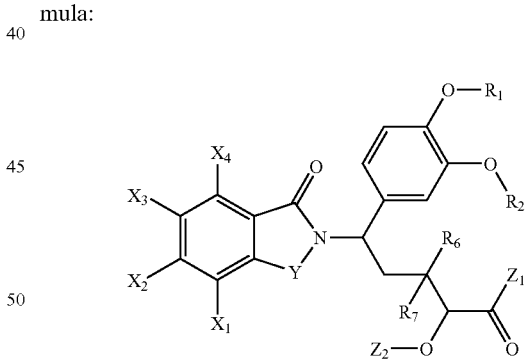

wherein:
Y is —C(O)—, —CH$_2$, —CH$_2$C(O)— or SO$_2$;
R$_1$ and R$_2$ are independently C$_{1-8}$-alkyl, CF$_2$H, CF$_3$, CH$_2$CHF$_2$, cycloalkyl, or (C$_{1-8}$-alkyl)cycloalkyl;
Z$_1$ is H, C$_{1-6}$-alkyl, —NH$_2$ —NR$_3$R$_4$ or OR$_5$;
Z$_2$ is H or C(O)R$_5$;
X$_1$, X$_2$, X$_3$ and X$_4$ are each independent H, halogen, NO$_2$, OR$_3$, CF$_3$, C$_{1-6}$-alkyl, (C$_{0-4}$-alkyl)-(C$_{3-6}$-cycloalkyl), (C$_{0-4}$-alkyl)-N—(R$_8$R$_9$), (C$_{0-4}$-alkyl)-NHC(O)—(R$_8$), (C$_{0-4}$-alkyl)-NHC(O)CH(R$_8$)(R$_9$), (C$_{0-4}$-alkyl)-NHC(O)N(R$_8$R$_9$), (C$_{0-4}$-alkyl)-NHC(O)O(R$_8$), (C$_{0-4}$-alkyl)-O—R$_8$, (C$_{0-4}$-alkyl)-imidazolyl, (C$_{0-4}$-alkyl)-pyrrolyl, (C$_{0-4}$-alkyl)-oxadiazolyl, (C$_{0-4}$-alkyl)-triazolyl or (C$_{0-4}$-alkyl)-heterocycle;

R₃, R₄, and R₅ are each independently H, $C_{1-6}$-alkyl, O—$C_{1-6}$-alkyl, phenyl, benzyl, or aryl;

R₆ and R₇ are independently H or $C_{1-6}$-alkyl;

R₈ and R₉ are each independently H, $C_{1-9}$-alkyl, $C_{3-6}$-cycloalkyl, ($C_{1-6}$-alkyl)-($C_{3-6}$-cycloalkyl), ($C_{0-6}$-alkyl)-N (R₄R₅), ($C_{1-6}$-alkyl)-OR₅, phenyl, benzyl, aryl, piperidinyl, piperizinyl, pyrolidinyl, morpholino, or $C_{3-7}$-heterocycloalkyl; or a pharmaceutically acceptable salt, solvate, hydrate, stereoisomer, clathrate, or prodrug thereof.

Specific selective cytokine inhibitory drugs include, but are not limited to:

2-[1(-3-ethoxy-4-methoxyphenyl)-2-methyl-sulfonyl-ethyl]isoindolin-1-one;

2-[1-(3-ethoxy-4-methoxyphenyl)-2-(N,N-dimethyl-aminosulfonyl)ethyl]isoindolin-1-one;

2-[1-(3-ethoxy-4-methoxyphenyl)-2-methyl-sulfonyl-ethyl]isoindoline-1,3-dione;

2-[1-(3-ethoxy-4-methoxyphenyl)-2-methyl-sulfonyl-ethyl]-5-nitro-isoindoline-1,3-dione;

2-[1-(3-ethoxy-4-methoxyphenyl)-2-methyl-sulfonyl-ethyl]-4-nitroisoindoline-1,3-dione;

2-[1-(3-ethoxy-4-methoxyphenyl)-2-methylsulfonyl-ethyl]-4-aminoisoindoline-1,3-dione;

2-[1-(3-ethoxy-4-methoxyphenyl)-2-methylsulfonyl-ethyl]-5-methylisoindoline-1,3-dione;

2-[1-(3-ethoxy-4-methoxyphenyl)-2-methylsulfonyl-ethyl]-5-acetamidoisoindoline-1,3-dione;

2-[1-(3-ethoxy-4-methoxyphenyl)-2-methylsulfonyl-ethyl]-4-dimethylaminoisondoline-1,3-dione;

2-[1-(3-ethoxy-4-methoxyphenyl)-2-methylsulfonyl-ethyl]-5-dimethylaminoisoindoline-1,3-dione;

2-[1-(3-ethoxy-4-methoxyphenyl)-2-methylsulfonyl-ethyl]benzo[e]isoindoline-1,3-dione;

2-[1-(3-ethoxy-4-methoxyphenyl)-2-methylsulfonyl-ethyl]-4-methoxyisoindoline-1,3-dione;

1-(3-cyclopentyloxy-4-methoxyphenyl)-2-methylsulfonylethyl-amine;

2-[1-(3-cyclopentyloxy-4-methoxyphenyl)-2-methylsulfonylethyl]isoindoline-1,3-dione; and 2-[1-(3-cyclopentyloxy-4-methoxyphenyl)-2-methylsulfonylethyl]-4-dimethylaminoisoindoline-1,3-dione.

Additional selective cytokine inhibitory drugs include the enantiomerically pure compounds disclosed in U.S. patent application Ser. No. 10/392,195 filed on Mar. 19, 2003; international patent application no. PCT/US03/0873, filed on Mar. 20, 2003; U.S. provisional patent application Nos. 60/438,450 and 60/438,448 to G. Muller et al., both of which were filed on Jan. 7, 2003; and U.S. provisional patent application No. 60/452,460 to G. Muller et al. filed on Mar. 5, 2003, all of which are incorporated herein by reference. Preferred compounds include an enantiomer of 2-[1-(3-ethoxy-4-methoxyphenyl)-2-methylsulfonylethyl]-4-acetylaminoisoindoline-1,3-dione and an enantiomer of 3-(3,4-dimethoxy-phenyl)-3-(1-oxo-1,3-dihydro-isoindol-2-yl)-propionamide.

Preferred selective cytokine inhibitory drugs used in the invention are 3-(3,4dimethoxy-phenyl)-3-(1-oxo-1,3-dihydro-isoindol-2-yl)-propionamide and cyclopropanecarboxylic acid {2-[1-(3-ethoxy-4-methoxy-phenyl)-2-methanesulfonyl-ethyl]-3-oxo-2,3-dihydro-1H-isoindol-4-yl}-amide, which are available from Celgene Corp., Warren, N.J. 3-(3,4-Dimethoxy-phenyl)-3-(1-oxo-1,3-dihydro-isoindol-2-yl)-propionamide has the following chemical structure:

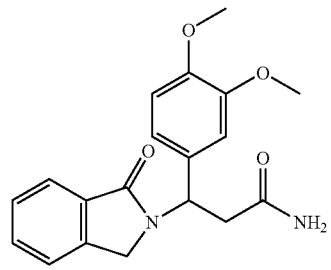

Cyclopropanecarboxylic acid {2-[1-(3-ethoxy-4-methoxyphenyl)-methanesulfonyl-ethyl]-3-oxo-2,3-dihydro-1H-isoindol-4-yl}-amide has the following chemical structure:

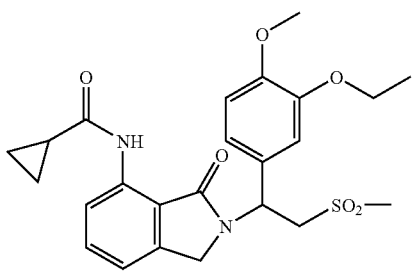

Compounds of the invention can either be commercially purchased or prepared according to the methods described in the patents or patent publications disclosed herein. Further, optically pure compositions can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases known in the art, which include, for example, hydrochloric acid, hydrobromic acid, phosphoric acid, sulfuric acid, methanesulfonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of selective cytokine inhibitory drugs that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of a selective cytokine inhibitory drug that comprise —NO, —NO$_2$, —ONO, or —ONO$_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elsevier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," and "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, 1 5 hydroxyalkylamines, heterocyclic and heteroaromatic amines, and polyether amines.

Various selective cytokine inhibitory drugs contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of selective cytokine inhibitory drugs may be used in methods and compositions of the invention. The purified (R) or (S) enantiomers of the specific compounds disclosed herein may be used substantially free of its other enantiomer.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound.

As used herein and unless otherwise indicated, the term "enantiomerically pure" means a stereomerically pure composition of a compound having one chiral center. Similarly, the term "enantiomerically enriched" means a stereomerically enriched composition of a compound having one chiral center.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Second Active Agents

A second active agent can be used in the methods and compositions of the invention together with a selective cytokine inhibitory drug. In a preferred embodiment, the second active agent is capable of inhibiting or relieving macular damaging conditions, providing antiangiogenesis or anti-inflammatory effects, or ensuring patient comfort.

Examples of second active agents include, but are not limited to, steroids, light sensitizers, integrins, antioxidants, interferons, xanthine derivatives, growth hormones, neutrotrophic factors, regulators of neovascularization, anti-VEGF antibodies, prostaglandins, antibiotics, phytoestrogens, anti-inflammatory compounds, antiangiogenesis compounds, other therapeutics known to inhibit or relieve a symptom of MD, and pharmaceutically acceptable salts, solvates, hydrates, stereoisomers, clathrates, prodrugs and pharmacologically active metabolites thereof. In certain embodiments, the second active agent is verteporfin, purlytin, an angiostatic steroid, rhuFab, interferon-2α, or pentoxifylline.

Examples of light sensitizers include, but are not limited to, verteporfin, tin etiopurpurin and motexafin lutetium. Verteporfin can be used to treat wet MD. Cour, M., et al., *Drugs Aging* 19:101-133 (2002). Verteporfin is a blood-vessel-blocking photoreactive dye that may be administered via injection.

Examples of xanthine derivatives include, but are not limited to, pentoxyfylline.

Examples of anti-VEGF antibodies include, but are not limited to, rhuFab.

Examples of steroids include, but are not limited to, 9-fluoro-11,21-dihydroxy-16,17-1-methylethylidinebis (oxy)pregna-1,4-diene-3,20-dione.

Examples of prostaglandin F$_2$a derivatives include, but are not limited to, latanoprost (see U.S. Pat. No. 6,225,348, which is incorporated by reference herein in its entirety).

Examples of antibiotics include, but are not limited to, tetracycline and its derivatives, rifamycin and its derivatives, macrolides, and metronidazole (see U.S. Pat. Nos. 6,218,369 and 6,015,803, the entireties of which are incorporated by reference herein).

Examples of phytoestrogens include, but are not limited to, genistein, genistin, 6'-O-Mal genistin, 6'-O-Ac genistin, daidzein, daidzin, 6'-O-Mal daidzin, 6'-O-Ac daidzin, glycitein, glycitin, 6'-O-Mal glycitin, biochanin A, formononetin, and a mixture thereof (see U.S. Pat. No. 6,001,368, which is incorporated by reference herein in its entirety).

Examples of anti-inflammatory agents include, but are not limited to, triamcinolone acetomide and dexamethasone (see U.S. Pat. No. 5,770,589, which is incorporated by reference herein in its entirety).

Examples of antiangiogenesis compounds include, but are not limited to, thalidomide and immunomodulatory compounds (IMiDs™, Celgene Corp., N.J.).

Examples of interferons include, but are not limited to, interferon-2α another embodiment, the second active agent is glutathione (see U.S. Pat. No. 5,632,984, which is incorporate by reference herein in its entirety).

Examples of growth hormones include, but are not limited to, basic fibroblast growth factor (bFGF) and transforming growth factor b (TGF-b).

Examples of neurotrophic factors include, but are not limited to, brain-derived neurotrophic factor (BDNF).

Examples of regulators of neovascularization include, but are not limited to, plasminogen activator factor type 2 (PAI-2).

Additional drugs which may be used for the treatment of MD include, but are not limited to, EYE101 (Eyetech Pharmaceuticals), LY333531 (Eli Lilly), Miravant and RETIS-ERT implant (Bausch & Lomb).

4.3 Methods for Treatment and Prevention

This invention encompasses methods of preventing, treating and/or managing various types of MD.

As used herein, unless otherwise specified, the terms "preventing MD," "treating MD" and "managing MD" include, but are not limited to, inhibiting or reducing the severity of one or more symptoms associated with MD. Symptoms associated with MD and related syndromes include, but are not limited to, drusen rounded whitish-yellowish spots in the fundus, submacular disciform scar tissue, choroidal neovascularisation, retinal pigment epithelium detachment, atrophy of retinal pigment epithelium, abnormal blood vessels stemming from the choroid (the blood vessel-rich tissue layer just beneath the retina), a blurry or distorted area of vision, a central blind spot, pigmentary abnormalities, a continuous layer of fine granular material deposited in the inner part of Bruch's membrane, and a thickening and decreased permeability of Bruch's membrane.

As used herein, unless otherwise specified, the term "treating MD" refers to the administration of a compound or other additional active agent after the onset of symptoms of MD, whereas "preventing" refers to the administration prior to the onset of symptoms, particularly to patients at risk of MD. Examples of patients at risk of MD include, but are not limited to, the elderly over the age of 60, and patients suffering from diseases such as, but not limited to, diabetes and leprosy (e.g., ENL). Patients with a familial history of MD are also preferred candidates for preventive regimens. As used herein and unless otherwise indicated, the term "managing MD" encompasses preventing the recurrence of MD in a patient who had suffered from MD, and/or lengthening the time that a patient who had suffered from MD remains in remission.

The invention encompasses methods of treating, preventing and managing MD and related syndromes in patients with various stages and specific types of the disease, including, but not limited to, those referred to as wet MD, dry MD, age-related maculopathy (ARM), choroidal neovascularisation (CNVM), retinal pigment epithelium detachment (PED), and atrophy of retinal pigment epithelium (RPE). It further encompasses methods of treating patients who have been previously treated for MD, are non-responsive to standard drug and non-drug-based MD treatments, as well as patients who have not previously been treated for MD. Because patients with MD have heterogenous clinical manifestations and varying clinical outcomes, the treatment given to a patient may vary, depending on his/her prognosis. The skilled clinician will be able to readily determine without undue experimentation specific secondary agents and treatments that can be effectively used to treat an individual patient.

Methods encompassed by this invention comprise administering one or more selective cytokine inhibitory drugs, or a pharmaceutically acceptable salt, solvate, hydrate, stereoisomer, clathrate, or prodrug thereof to a patient suffering, or likely to suffer, from MD.

In one embodiment, the recommended daily dose range of a selective cytokine inhibitory drug is from about 1 mg to about 10,000 mg per day, given as a single once-a-day dose, or preferably in divided doses throughout a day. More specifically, the daily dose is administered twice daily in equally divided doses. Specific daily dose ranges are from about 1 mg to about 5,000 mg per day, from about 10 mg to about 2,500 mg per day, from about 100 mg to about 800 mg per day, from about 100 mg to about 1,200 mg per day, or from about 25 mg to about 2,500 mg per day. In managing a patient, the therapy should be initiated at a lower dose, perhaps about 1 mg to about 2,500 mg, and increased if necessary up to about 200 mg to about 5,000 mg per day as either a single dose or divided doses, depending on the patient's global response. In a particular embodiment, 3-(3,4-dimethoxy-phenyl)-3-(1-oxo-1,3-dihydro-isoindol-2-yl)-propionamide is administered in an amount of about 400, 800, 1,200, 2,500, 5,000 or 10,000 mg a day as two divided doses. The treatment lasts about two to about twenty weeks, about four to about sixteen weeks, about eight to about twelve weeks, until the desired therapeutic effect is achieved, or chronically to maintain the desired effect.

4.3.1 Combination Therapy With A Second Active Agent

Specific methods of the invention comprise administering a selective cytokine inhibitory drug, or a pharmaceutically acceptable salt, solvate, hydrate, stereoisomer, clathrate, or prodrug thereof, in combination with a second active agent or active ingredient. Examples of selective cytokine inhibitory drugs are disclosed herein (see, e.g., section 4.1); and examples of second active agents are also disclosed herein (see, e.g., section 4.2).

Administration of a selective cytokine inhibitory drug and an optional second active agent to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for selective cytokine inhibitory drugs is oral or ophthalmic. Preferred routes of administration for the second active agents or ingredients of the invention are known to those of ordinary skill in the art, for example in *Physicians' Desk Reference* (57th ed., 2003).

In one embodiment, the second active agent is administered orally, intravenously, intramuscularly, subcutaneously, mucosally, topically, or transdermally and once or twice daily in an amount of from about 1 to about 2,500 mg, from about 1 mg to about 2,000 mg, from about 10 mg to about 1,500 mg, from about 50 mg to about 1,000 mg, from about 100 mg to about 750 mg, or from about 250 mg to about 500 mg.

In further embodiments, the second active agent is administered weekly, monthly, bi-monthly or yearly. The specific amount of the second active agent can depend on the specific agent used, the type of MD being treated or prevented, the severity and stage of MD, and the amounts of selective cytokine inhibitory drugs and any optional other agent(s) concurrently administered to the patient. In a particular embodiment, the second active agent is a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof.

4.3.2 Use With Surgical Intervention

This invention encompasses a method of treating, preventing and/or managing MD, which comprises administering a selective cytokine inhibitory drug, or a pharmaceutically acceptable salt, solvate, hydrate, stereoisomer, clathrate, or prodrug thereof, in conjunction with (e.g. before, during, or after) surgical intervention. Examples of surgical intervention include, but are not limited to, light or laser therapy, radiation therapy, retinal pigment epithelium transplantation, and foveal translocation.

The combined use of the selective cytokine inhibitory drugs and surgical intervention provides a unique treatment regimen that can be unexpectedly effective in certain patients. Without being limited by theory, it is believed that selective cytokine inhibitory drugs may provide additive or synergistic effects when given concurrently with surgical intervention.

In a specific embodiment, the invention encompasses methods for treating, preventing, and/or managing MD, comprising administering to a patient in need thereof an effective amount of a selective cytokine inhibitory drug, or a pharmaceutically acceptable salt, solvate, hydrate, stereoisomer, clathrate or prodrug thereof, in combination with light or laser therapy. Examples of light or laser therapy include, but are not limited to, laser photocoagulation therapy or photodynamic therapy.

The selective cytokine inhibitory drug can be administered simultaneously or sequentially with the surgical intervention. In one embodiment, the selective cytokine inhibitory drug is administered prior to light or laser therapy. In another embodiment, the selective cytokine inhibitory drug is administered after light or laser therapy. In one embodiment, the selective cytokine inhibitory drug is administered during light or laser therapy. The compound may be administered at least four weeks prior, two weeks prior, one week prior, or just prior to laser surgery, or at the time or just after the surgery for a total treatment of about 12-16 weeks.

4.3.3 Cycling Therapy

In certain embodiments, the prophylactic or therapeutic agents are cyclically administered to a patient. Cycling therapy involves the administration of a first agent for a period of time, followed by the administration of the agent and/or a second agent for a period of time and repeating this sequential administration. Cycling therapy can reduce the development of resistance to one or more of the therapies, avoid or reduce the side effects of one of the therapies, and/or improves the efficacy of the treatment.

In a specific embodiment, prophylactic or therapeutic agents are administered in a cycle of about six months, about once or twice every day. One cycle can comprise the administration of a therapeutic or prophylactic agent and at least one or three weeks of rest. The number of cycles administered can be from about one to about 12 cycles, about two to about 10 cycles, or about two to about eight cycles.

4.4 Pharmaceutical Compositions and Single Unit Dosage Forms

Pharmaceutical compositions can be used in the preparation of individual, single unit dosage forms. Pharmaceutical compositions and dosage forms of the invention comprise selective cytokine inhibitory drugs, or pharmaceutically acceptable salts, solvates, hydrates, stereoisomers, clathrates, or prodrugs thereof. Pharmaceutical compositions and dosage forms of the invention can further comprise one or more excipients.

Pharmaceutical compositions and dosage forms of the invention can also comprise one or more additional active agents. Consequently, pharmaceutical compositions and dosage forms of the invention comprise the active agents disclosed herein (e.g., selective cytokine inhibitory drugs, or a pharmaceutically acceptable salt, solvate, hydrate, stereoisomer, clathrate, or prodrug thereof, and a second active agent). Examples of optional additional active agents are disclosed herein (see, e.g., section 4.2).

Single unit dosage forms of the invention are suitable for oral, mucosal (e.g., nasal, sublingual, vaginal, buccal, or rectal), or parenteral (e.g., subcutaneous, intravenous, bolus injection, intramuscular, or intraarterial), topical (e.g., eye drops), ophthalmic, transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); eye drops; gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active agents it comprises than a dosage form used in the chronic treatment of the same disease. Similarly, a parenteral dosage form may contain smaller amounts of one or more of the active agents it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active agents in the dosage form. For example, the decomposition of some active agents may be accelerated by some excipients such as lactose, or when exposed to water. Active agents that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active agent.

Lactose-free compositions of the invention can comprise excipients that are well known in the art and are listed, for example, in the *U.S. Pharmacopeia* (USP) 25-NF20 (2002). In general, lactose-free compositions comprise active agents, a binder/filler, and a lubricant in pharmaceutically compatible and pharmaceutically acceptable amounts. Preferred lactose-free dosage forms comprise active agents, microcrystalline cellulose, pre-gelatinized starch, and magnesium stearate.

This invention further encompasses anhydrous pharmaceutical compositions and dosage forms comprising active agents, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active agent that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active agent will decompose. Such compounds, which are referred to herein as "stabilizers," include, but are not limited to, antioxidants such as ascorbic acid, pH buffers, or salt buffers.

Like the amounts and types of excipients, the amounts and specific types of active agents in a dosage form may differ depending on factors such as, but not limited to, the route by which it is to be administered to patients. However, typical dosage forms comprise a selective cytokine inhibitory drug, or a pharmaceutically acceptable salt, solvate, hydrate, stereoisomer, clathrate, or prodrug thereof in an amount of from about 1 to about 10,000 mg. Typical dosage forms comprise a selective cytokine inhibitory drug, or a pharmaceutically acceptable salt, solvate, hydrate, stereoisomer, clathrate, or prodrug thereof in an amount of about 1, 2, 5, 10, 25, 50, 100, 200, 400, 800, 1,200, 2,500, 5,000 or 10,000 mg. In a particular embodiment, a preferred dosage form comprises 3-(3,4-dimethoxy-phenyl)-3-(1-oxo-1,3-dihydro-isoindol-2-yl)-propionamide in an amount of about 400, 800 or 1,200 mg. Typical dosage forms comprise the second active agent in an amount of form about 1 to about 2,500 mg, from about 1 mg to about 2,000 mg, from about 10 mg to about 1,500 mg, from about 50 mg to about 1,000 mg, from about 100 mg to about 750 mg, or from about 250 mg to about 500 mg. Of course, the specific amount of the second active agent will depend on the specific agent used, the type of MD being treated or managed, and the amount(s) of selective cytokine inhibitory drug and any optional additional active agents concurrently administered to the patient.

4.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active agents, and may be prepared by methods of pharmacy well known to those skilled in the art. See generally, *Remington's Pharmaceutical Sciences*, 18th ed., Mack Publishing, Easton Pa. (1990).

Typical oral dosage forms are prepared by combining the active agents in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active agents with liquid carriers, finely divided solid carriers, or both, and then shaping the product into the desired presentation if necessary.

For example, a tablet can be prepared by compression or molding. Compressed tablets can be prepared by compressing in a suitable machine the active agents in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active agents should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form comprises a selective cytokine inhibitory drug, anhydrous lactose, microcrystalline cellulose, polyvinylpyrrolidone, stearic acid, colloidal anhydrous silica, and gelatin.

4.4.2 Delayed Release Dosage Forms

Active agents of the invention can be administered by controlled release means or by delivery devices that are well known to those of ordinary skill in the art. Examples include, but are not limited to, those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active agent) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active agent can be stimulated by various conditions including, but not limited to, pH, temperature, enzymes, water, or other physiological conditions or compounds.

4.4.3 Parenteral Dosage Forms

Parenteral dosage forms can be administered to patients by various routes including, but not limited to, intravitreal, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active agents disclosed herein can also be incorporated into the parenteral dosage forms of the invention. For example, cyclodextrin and its derivatives can be used to increase the solubility of selective cytokine inhibitory drugs and its derivatives. See, e.g., U.S. Pat. No. 5,134,127, which is incorporated herein by reference.

4.4.4 Topical And Mucosal Dosage Forms

Topical and mucosal dosage forms of the invention include, but are not limited to, eye drops, sprays, aerosols, solutions, emulsions, suspensions, or other forms known to one of skill in the art. See, e.g., *Remington's Pharmaceutical Sciences*, 16$^{th}$ and 18$^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 16$^{th}$ and 18$^{th}$ eds., Mack Publishing, Easton Pa. (1980 & 1990).

The pH of a pharmaceutical composition or dosage form may also be adjusted to improve delivery of one or more active agents. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active agents so as to improve delivery. In this regard, stearates can serve as a lipid vehicle for the formulation, as an emulsifying agent or surfactant, and as a delivery-enhancing or penetration-enhancing agent. Different salts, hydrates or solvates of the active agents can be used to further adjust the properties of the resulting composition.

4.4.5 Kits

Typically, active agents of the invention are preferably not administered to a patient at the same time or by the same route of administration. This invention therefore encompasses kits which, when used by the medical practitioner, can simplify the administration of appropriate amounts of active agents to a patient.

A typical kit of the invention comprises a dosage form of a selective cytokine inhibitory drug, or a pharmaceutically acceptable salt, solvate, hydrate, stereoisomer, prodrug, or clathrate thereof. Kits encompassed by this invention can further comprise one or more additional active agents or a combination thereof. Examples of the additional active agents are disclosed herein. (See, e.g., section 4.2).

Kits of the invention can further comprise devices that are used to administer the active agents. Examples of such devices include, but are not limited to, syringes, drip bags, patches, and inhalers. A kit of the invention can further comprise an Amsler grid useful for detecting or diagnosing MD.

Kits of the invention can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

The following examples are intended to further illustrate the invention without limiting its scope.

5.1 In Vitro Pharmacology Studies

One of the biological effects typically exerted by selective cytokine inhibitory drugs is the reduction of synthesis of TNF-α. Specific selective cytokine inhibitory drugs enhance the degradation of TNF-α mRNA. TNF-α may play a pathological role in macular degeneration.

In a specific embodiment, the pharmacological properties of 3-(3,4-dimethoxy-phenyl)-3-(1-oxo-1,3-dihydro-isoindol-2-yl)-propionamide are characterized in in vitro studies. Studies examine the effects of the compound on the production of various cytokines. Inhibition of TNF-α production following LPS-stimulation of human PBMC and human whole blood by the compound is investigated in vitro. In vitro studies suggest a pharmacological activity profile for 3-(3,4-dimethoxy-phenyl)-3-(1-oxo-1,3-dihydro-isoindol-2-yl)-propionamide is five to fifty times more potent than thalidomide. The pharmacological effects of 3-(3,4-dimethoxy-phenyl)-3-(1-oxo-1,3-dihydro-isoindol-2-yl)-propionamide may derive from its action as an inhibitor of the generation of inflammatory cytokines.

5.2 Clinical Studies in Patients with MD

Selective cytokine inhibitory drugs of the invention are administered in an amount of about 20 to about 1,200 mg per day to patients with macular degeneration. In a specific embodiment, clinical studies are performed with forty patients with macular degeneration, who are divided into two groups. The first group receives conventional treatment for closing the leaking choroidal vessels (characteristic of this disease) by photodynamic therapy with verteporfin. Ophthalmol 1999 (117): 1329-1345. The second group receives the same conventional therapy with verteporfin and (+)-2-[1-(3-ethoxy-4 methoxy-phenyl)-2-methylsulfonylethyl]-4 acetylaminoisoindoline 1,3-dione in an amount of about 20 mg/day as an adjuvant for 20 weeks.

The neovascular cascade is sufficiently hindered in the group receiving (+)-2-[1-(3-ethoxy-4 methoxyphenyl)-2-methylsulfonylethyl]-4 acetylaminoisoindoline 1,3-dione to indefinitely prolong the effects of the photodynamic therapy. However, the first group without (+)-2-[1-(3-ethoxy-4 methoxyphenyl)-2-methylsulfonylethyl]-4 acetylaminoisoindoline 1,3-dione experiences progressive reperfusion of the ablated vessels several weeks after treatment. Progressive visual loss follows which requires the photodynamic therapy to be repeated.

In another preferred embodiment, (+)-2-[1-(3-ethoxy-4 methoxyphenyl)-2-methylsulfonylethyl]-4 acetylaminoisoindoline 1,3-dione is administered in an amount of about 1 to about 200 mg/day, preferably about 10 to about 50 mg/day, or a greater dose, generally about 1.5 to 2.5 times the daily dose every other day. The adjuvant therapy is applicable to other types of conventional therapy used to treat or prevent MD including, but not limited to, surgical intervention including laser photocoagulation.

Embodiments of the invention described herein are only illustrative of the scope of the invention. A number of references have been cited herein, the entire contents of which have been incorporated by reference herein.

What is claimed is:

1. A method of treating macular degeneration, which comprises administering to a patient having macular degeneration a therapeutically effective amount of cyclopropyl-N-{2-[(1S)-1-(3-ethoxy-4-methoxyphenyl)-2-methylsulfonyl)ethyl]-3-oxoisoindoline-4-yl}carboxamide, which has the following structure:

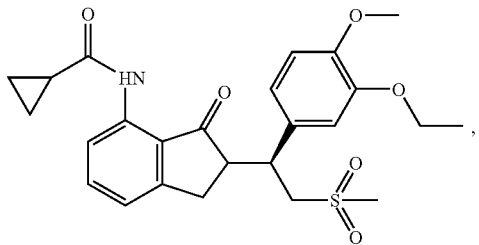

or a pharmaceutically acceptable salt, or solvate thereof.

2. The method of claim 1, which further comprises administering to the patient a therapeutically effective amount of a second active agent.

3. The method of claim 2, wherein the second active agent is a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound.

4. The method of claim 2, wherein the second active agent is thalidomide, verteporfin, purlytin, an angiostatic steroid, rhuFab, interferon-2α or pentoxifylline, or a pharmaceutically acceptable salt, solvate, or stereoisomer thereof.

5. The method of claim 3, wherein the antiangiogenesis compound is thalidomide.

6. The method of claim 1, wherein the macular degeneration is wet macular degeneration, dry macular degeneration, age-related macular degeneration, age-related maculopathy, choroidal neovascularisation, retinal pigment epithelium detachment, atrophy of retinal pigment epithelium, Best's disease, vitelliform, Stargardt's disease, juvenile macular dystrophy, fundus flavimaculatus, Behr's disease, Sorsby's disease, Doyne's disease, honeycomb dystrophy, or macular damaging condition.

7. The method of claim 1, wherein the compound is stereomerically pure.

8. A method of treating macular degeneration, which comprises administering to a patient having macular degeneration a therapeutically effective amount of cyclopropyl-N- {2-[(1S)-1-(3-ethoxy-4-methoxyphenyl)-2-(methylsulfonyl)-ethyl]-3-oxoisoindoline-4-yl}carboxamide, which has the following structure:

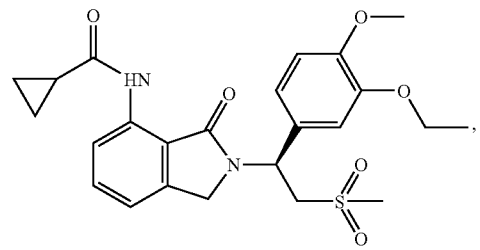

or a pharmaceutically acceptable salt, or solvate thereof, before, during or after surgical intervention directed at reducing or avoiding a symptom of macular degeneration in the patient.

9. The method of claim 8, wherein the surgical intervention is light therapy, laser therapy, radiation therapy, retinal pigment epithelium transplantation, or foveal translocation.

10. The method of claim 1, wherein the amount of cyclopropyl-N- {2-[(1S)-1-(3-ethoxy-4-methoxyphenyl)-2-(methylsulfonyl)-ethyl]-3oxoisoindoline-4-yl}carboxamide administered is from about 1 mg to about 5,000 mg per day.

11. The method of claim 1, wherein the amount of cyclopropyl-N- {2-[(1S)-1-(3-ethoxy-4-methoxyphenyl)-2-(methylsulfonyl)-ethyl]-3oxoisoindoline-4-yl}carboxamide administered is from about 10 mg to about 2,500 mg per day.

12. The method of claim 1, wherein the amount of cyclopropyl-N- {2-[(1S)-1-(3-ethoxy-4-methoxyphenyl)-2-(methylsulfonyl)-ethyl]-3oxoisoindoline-4-yl}carboxamide administered is from about 100 mg to about 1,200 mg per day.

13. The method of claim 1, wherein the amount of cyclopropyl-N-{2-[(1S)-1-(3-ethoxy-4-methoxyphenyl)-2-(methylsulfonyl)-ethyl]-3-oxoisoindoline-4-yl}carboxamide administered is from about 100 mg to about 800 mg per day.

* * * * *